United States Patent
Zapata

(10) Patent No.: US 8,517,976 B2
(45) Date of Patent: Aug. 27, 2013

(54) ABDOMINAL INSUFFLATOR AND PRINCIPAL TROCAR-CANNULA DEVICE

(76) Inventor: Helio Zapata, Chicago, IL (US)

(*) Notice: Subject to any disclaimer, the term of this patent is extended or adjusted under 35 U.S.C. 154(b) by 742 days.

(21) Appl. No.: 11/695,173

(22) Filed: Apr. 2, 2007

(65) Prior Publication Data

US 2007/0232988 A1   Oct. 4, 2007

Related U.S. Application Data

(63) Continuation-in-part of application No. 11/396,725, filed on Apr. 3, 2006, now abandoned.

(51) Int. Cl.
*A61M 37/00* (2006.01)
(52) U.S. Cl.
USPC ........................................ 604/26; 604/164.06
(58) Field of Classification Search
USPC .................. 604/26, 30, 23, 164.06
See application file for complete search history.

(56) References Cited

U.S. PATENT DOCUMENTS

| | | | |
|---|---|---|---|
| 3,993,079 A * | 11/1976 | Henriques de Gatztanondo | 604/164.01 |
| 4,191,191 A * | 3/1980 | Auburn | 604/164.06 |
| 5,630,805 A * | 5/1997 | Ternamian | 604/274 |
| 5,941,852 A * | 8/1999 | Dunlap et al. | 604/164.11 |
| 6,053,925 A * | 4/2000 | Barnhart | 606/116 |
| 6,921,387 B2 * | 7/2005 | Camrud | 604/164.06 |
| 7,153,319 B1 * | 12/2006 | Haberland et al. | 606/185 |
| 2006/0178671 A1 * | 8/2006 | Canady | 606/49 |

OTHER PUBLICATIONS

Stepanian, "Computer Analysis of 5-mm Trocars: Dilating Tip Versus Non-Shielded Bladed", Journal of Minimally Invasive Gynecology, vol. 14, 2007, pp. 176-177.

* cited by examiner

*Primary Examiner* — Kevin C Sirmons
*Assistant Examiner* — Deanna K Hall
(74) *Attorney, Agent, or Firm* — Barnes & Thornburg LLP

(57) ABSTRACT

A hollow plastic cannula with plunger having a funnel shape entrance at one side and a sharp slant cut on the other. A hollow polyethylene catheter is shaped to fit within the cannula once inserted in the abdomen. The present invention is a means of performing an error-free abdominal insufflation for Laparoscopic procedures.

20 Claims, 12 Drawing Sheets

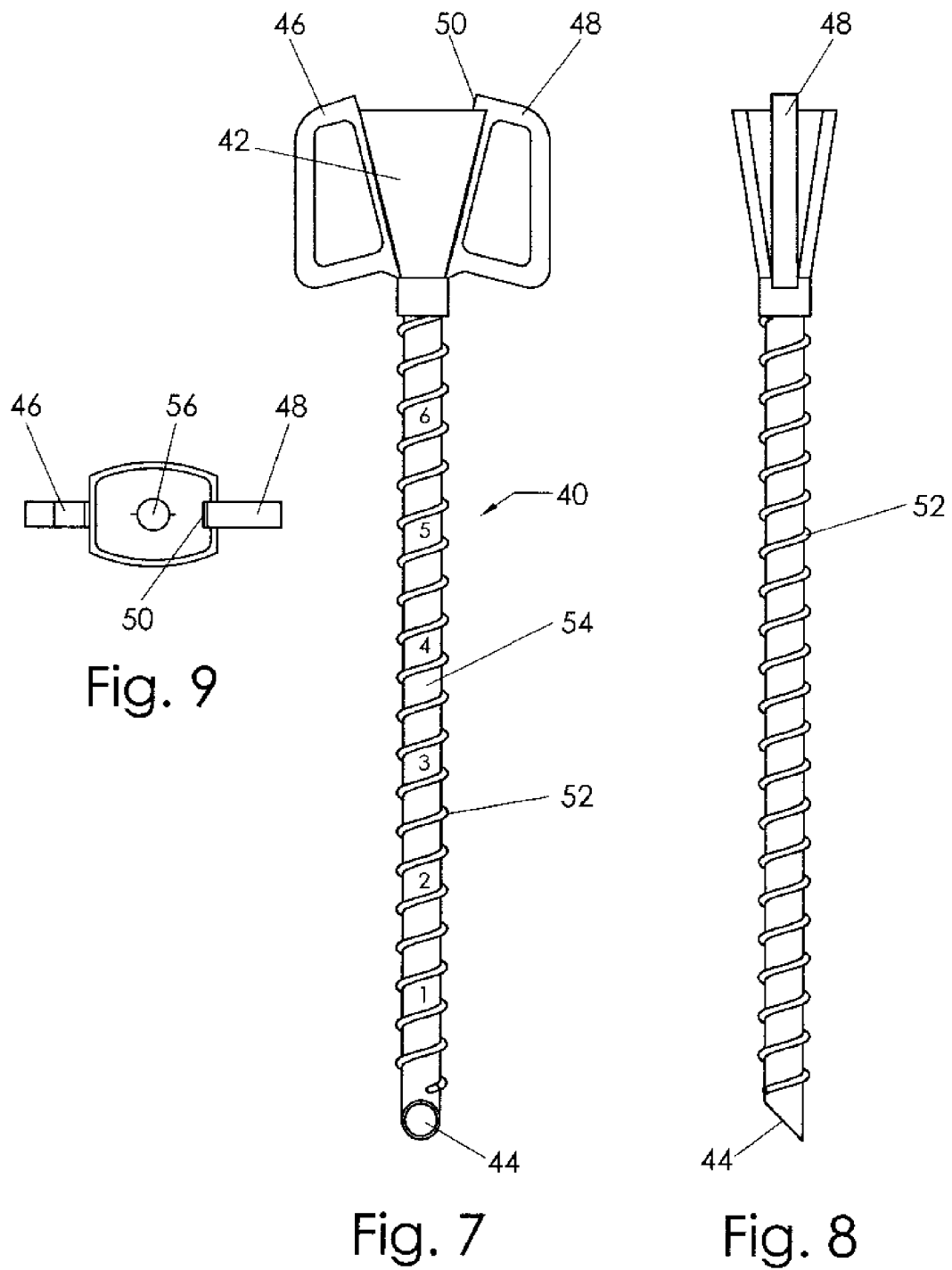

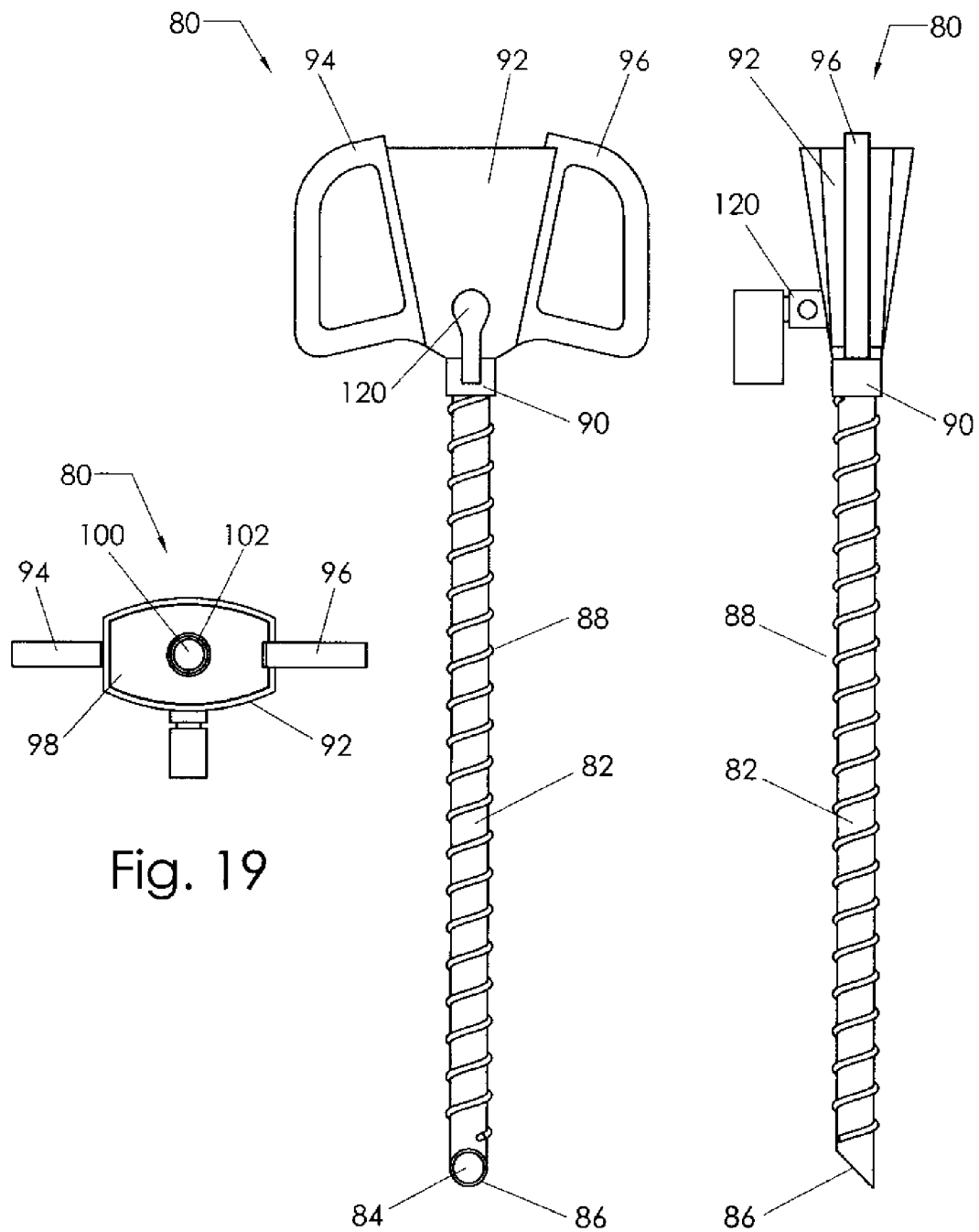

ABDOMINAL INSUFFLATOR AND PRINCIPAL TROCAR-CANNULA DEVICE

RELATED APPLICATION

This application is a continuation-in-part of U.S. patent application Ser. No. 11/396,725, filed Apr. 3, 2006 now abandoned.

BACKGROUND OF THE INVENTION

Laparoscopy is the operative procedure that allows the surgeon to view the abdominal cavity with a long rod-type scope (Laparoscope), to perform operations without the need of employing large incisions. The Laparoscope is inserted through a small incision around the navel. Before the Laparoscope can be inserted, the abdominal cavity has to be insufflated with $CO_2$ to allow the introduction of a large trocar (the Principal Trocar-Cannula Unit) which provides the portal for the introduction of the Laparoscope. To accomplish this initial phase of this procedure, to create a pneumo-peritoneum, the surgeon inserts in or around the navel a Veress needle. This is a rigid, metallic needle, of ten, twelve, fifteen or seventeen cm of length, and two mm in diameter. This needle is pushed through the anterior abdominal wall until it is several centimeters inside the abdominal cavity. If the needle is successfully placed into the free space of the abdominal cavity the process of insufflation proceeds uneventfully.

In order to ascertain that the Veress needle is inside the abdominal cavity, surgeons "test" the position of the needle employing various maneuvers. There are several such tests. One is "manometer test", which involves the connection of the Veress needle to the insufflating system and by pulling up the anterior abdominal wall with towel clips the operator observes if a negative pressure is registered in the system's manometer. Another maneuver is the "hanging drop test", which consists of placing water at the upper end of the Veress needle and seeing if the drop of water is sucked inside the needle by the vacuum in the abdominal cavity. A third test is the "hissing sound test", in which the operator turns the valve in the Veress needle to the off position and then opens it. He then lifts the anterior abdominal wall with towel clips to suck air from the needle into the abdominal cavity. He is supposed to hear the hissing sound of the air going inside the needle. Another test is injecting air inside the Veress needle with a syringe to see if it goes easy. An easy injection means the needle is in the abdominal cavity. Another test is the injection of a small amount of water. In this maneuver, the surgeon first aspirates the needle with a syringe. If no blood or bowel content is obtained, the surgeon then injects a small amount of sterile water and aspirates again. If the water is re-aspirated, it means that the operator is in an enclosed space, not the free space of the abdominal cavity. One more maneuver is the "double-click test". In this test, the operator should hear two distinct clicks as the needle traverses critical layers of the anterior abdominal wall. If this double-click is heard, it is reassuring that the needle is in the abdominal cavity. The most sensitive of all tests seems to be the detection of a high insufflating pressure in the laparoscopy system. Modern equipment is good in detecting unusually high pressure when the needle is not in the right place but even this last test is not free of frequent errors. This high-pressure indicator is not reliable and the creation of subcutaneous emphysema or pnemo-omentum may still occur in spite of a seemingly low pressure in the system.

Very often all of these testing maneuvers eventually fool the operator into believing that he or she is in the right place when, indeed, the needle is not in the free-space of the abdominal cavity but in the thickness of the anterior abdominal wall or hitting an intra-abdominal structure. None of these maneuvers guarantee successful access to the free space of the abdominal cavity. If insufflation is done when the Veress needle is within the thickness of the anterior abdominal wall, a subcutaneous emphysema is then created and, if not recognized immediately, it becomes of a significant size and subsequent attempts to inflate the abdominal cavity become increasingly more difficult.

After the insertion of the Veress needle, the initiation of the insufflation is started. Surgeons usually begin to inflate with a low flow of $CO_2$. After a wait of a few seconds the surgeon sees if the characteristic tympanic sound is heard on percussion of the abdomen, generally on all four quadrants of the anterior abdominal wall. During this waiting period he also perceives with his hand the typical drum-like resilience of the anterior abdominal wall on percussion when the cavity is filled with gas. The operator then proceeds to continue the insufflation at a high gas flow. The fact remains that before accurate abdominal insufflation is achieved, there is a good degree of anxiety created by the doubt, hesitancy, uncertainty and fear of failure that assails the surgeon because he is not absolutely sure that the tip of the needle is in the right place. This doubt prompts him to remove and re-insert the Veress needle until he is "reasonably" sure he is in the right space to cautiously let the insufflation begin.

To this day, the creation of unwanted subcutaneous emphysema remains a problem in Laparoscopic procedures. The more obese the patient is, the greater the chances of its occurrence. Besides the above-mentioned drawbacks, there are other complications associated with the Veress needle. One is the creation of pneumo-omentum, which is the instillation of $CO_2$ into the thickness of the omental flaps. Another complication is the accidental puncture of intestines or the injury to blood vessels. Because the Veress needle has to be inserted several centimeters inside the abdominal wall, if the patient is thin, the risk of accidental puncture of a major blood vessel is greatly increased. All textbooks of laparoscopy warn surgeons about the exceedingly close proximity of the anterior abdominal wall to the major vessels in these thin patients, particularly at the level of the navel, the site of insertion of the Veress needle.

In an effort to overcome these series of obstacles associated with the trans-abdominal insertion of the Veress needle, surgeons all over the world have tried other ways to access the abdominal cavity with the Veress needle. In obese patients they insert the Veress needle trans-vaginally to reach the cul-de-sac, or even directly through the fundus of the uterus. In some countries, the gas-less Laparoscopy has been introduced.

Various modifications to the Veress needle have been invented. One is the Veress-Frangenheim needle, which is double-barreled to permit insufflation while at the same time measure the pressure around the needle. Another is the Foures-Kuss needle, which has lateral holes that permit insufflation even if the needle tip is hitting an obstacle. None of these varieties is now in use, and furthermore, they are subject to the same failure of creating subcutaneous emphysema or injury to internal organs as the original Veress needle.

To avoid all the problems associated with the use of the Veress needle, Harrit Hasson in 1972 introduced the Open Laparoscopy. In this alternative, the Veress needle is entirely avoided and, instead, the abdominal cavity is entered in the traditional way via a small incision below the navel to allow the insertion of the trocar carrying the portal to the Laparoscope. Currently, however, the Veress needle is, by far, the preferred method being used but it is, unfortunately, not devoid of its attendant risk of failure due to misplacement of the needle in the thickness of the anterior abdominal wall or potential injury to internal structures.

The present invention solves easily, safely, quickly, and error-free, all the problems associated with the use of the Veress needle for abdominal insufflation for Laparoscopy, namely, the creation of subcutaneous emphysema or pneumo-omentum, and the risk of injury to intra-abdominal structures. If a safe and effective pneumo-peritoneum can be created by the invention, there is no need for open Laparoscopies.

Insertion of the large Principal Trocar-Cannula unit, once the abdomen is successfully inflated, is not devoid of difficulties and complications. These Principal Trocar-Cannula units have either sharp blades or sharp points at their tips. Insertion has to be done by forcibly pushing them through the anterior abdominal wall. It is literally a blind thrust of this unit well inside the abdominal cavity. Sometimes the insertion is difficult due to resistant abdominal walls, or it may go too fast inside the abdomen. It is a known fact that the force applied for the insertion has to be greater than the resistance of the inflated abdominal wall. Although complications with the insertion of the Principal Trocar-Cannula unit are significantly rare, when they occur they tend to be very serious.

SUMMARY OF THE INVENTION

The invention is first directed to an abdominal insufflator, comprising an elongated, hollow cannula having an inclined tip at one end, an open opposite end, and a plunger shaped to be engaged in and co-extensive with the cannula, the plunger having an inclined tip at one end and an engagement end shaped to conform to the open opposite end of the cannula. A system is provided for aligning the plunger when engaged within the cannula.

In accordance with the preferred form of this part of the invention, the open opposite end of the hollow cannula is funnel-shaped. Similarly, the engagement end of the plunger is funnel-shaped. The funnels are sized to fit within one another.

The aligning system comprises a notch in the open opposite end of the hollow cannula and a protrusion in the insertion end of the plunger. The protrusion is shaped to fit within the notch.

To facilitate utilization of the insufflator, a pair of grasping rings is located on opposite sides of the opened opposite end of the hollow cannula. A guide ring is formed at the engagement end of the plunger.

In the preferred form of this part of the invention, the abdominal insufflator is part of a system which includes a catheter which is shaped to fit within the hollow cannula. The catheter has a length considerably greater than that of the hollow cannula, and includes a flow control for gas control through the catheter.

The invention also includes an abdominal trocar, comprising an elongated, hollow cannula having an inclined tip at one end, an opposite end, and a plunger shaped to be engaged in and co-extensive with the cannula, the plunger having an inclined tip at one end and an engagement end shaped to conform to the opposite end of the cannula. A system is provided for aligning the plunger when engaged within the cannula. A valve system is provided at the opposite end.

In this form of the invention, the valve system includes an inlet in alignment with and shaped to be engaged by the plunger. The inlet comprises a normally-closed valve, which comprises a plunger-accommodating tube and a hinged lid engaging a seat to sealingly close the tube, and a spring urging the lid against the seat. The valve system also includes a normally-closed outlet valve.

In this form of the invention, the aligning system comprises a protrusion in the opposite end and a notch in the engagement end, with the protrusion being shaped to fit within the notch.

In both forms of the invention, the cannula may have an exterior insertion thread.

A system according to the invention comprises the combination of the abdominal insufflator and the abdominal trocar.

BRIEF DESCRIPTION OF THE DRAWINGS

FIG. 7 is an elevational view of the hard plastic cannula of a second form of the invention.

FIG. 8 is a side view of the cannula of FIG. 7.

FIG. 9 is a top plan view of the cannula of FIG. 7.

FIG. 17 is an elevational view of a plastic cannula for a trocar.

FIG. 18 is a side elevational view of the cannula of FIG. 17.

FIG. 19 is a top plan view of the cannula of FIG. 17.

DETAILED DESCRIPTION OF THE INVENTION

Figure 1:
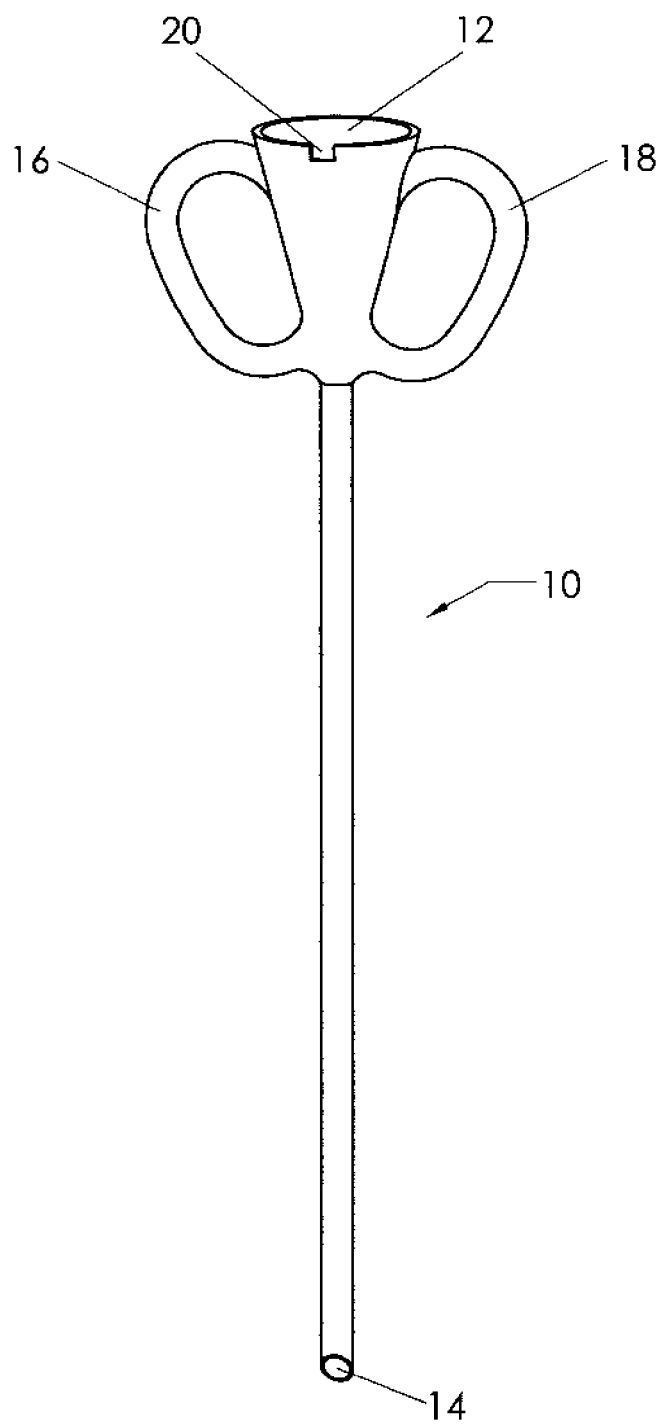
FIG. 1 is an oblique upper view of the hard plastic cannula of the invention.
Figure 2:
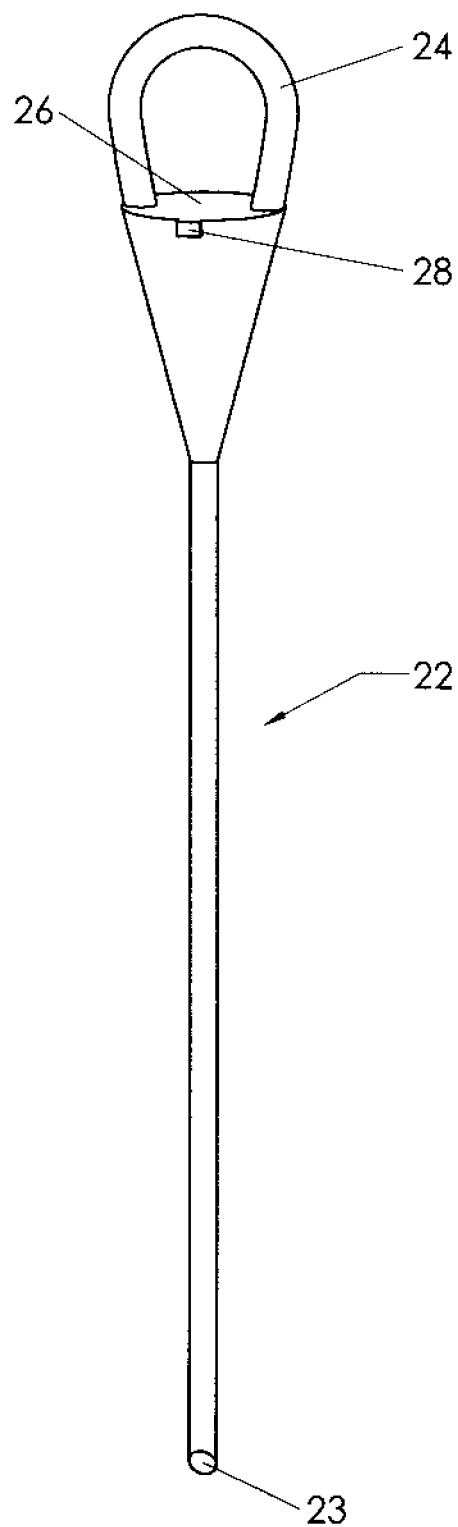
FIG. 2 is a panoramic view of the cannula's plunger.
Figure 3:
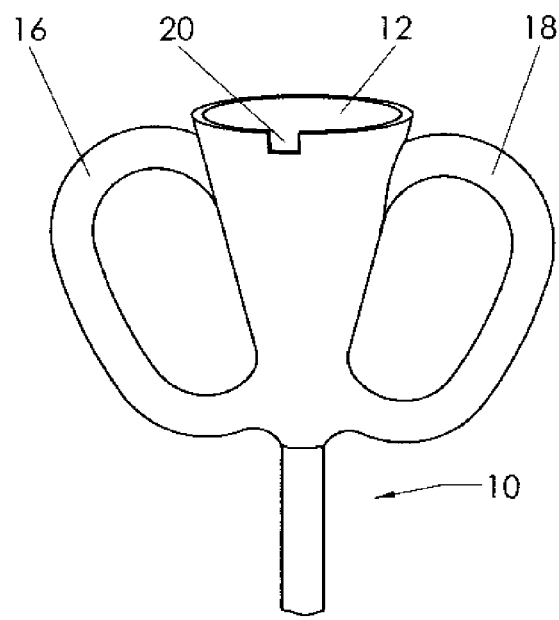
FIG. 3 is an enlarged view of the plastic cannula's funnel depicting the notch it bears in its outer edge.
Figure 4:
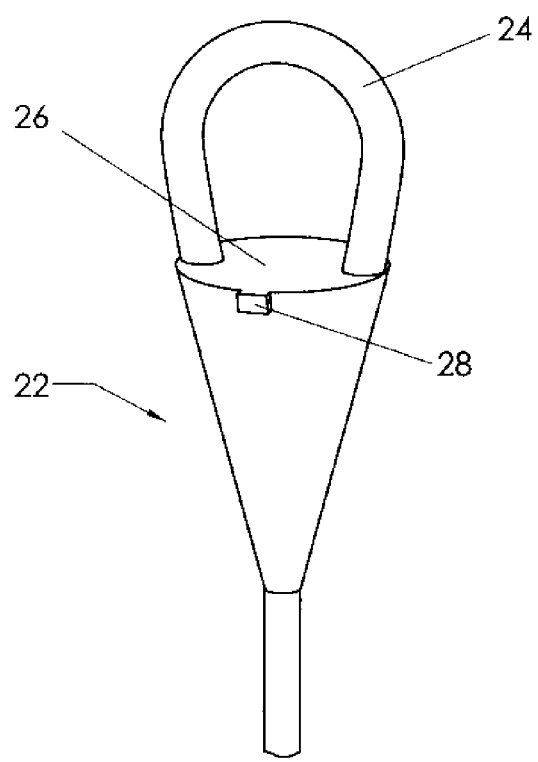
FIG. 4 is an enlarged view of the plunger's head showing the ring attached to its flat upper surface.
Figure 5:
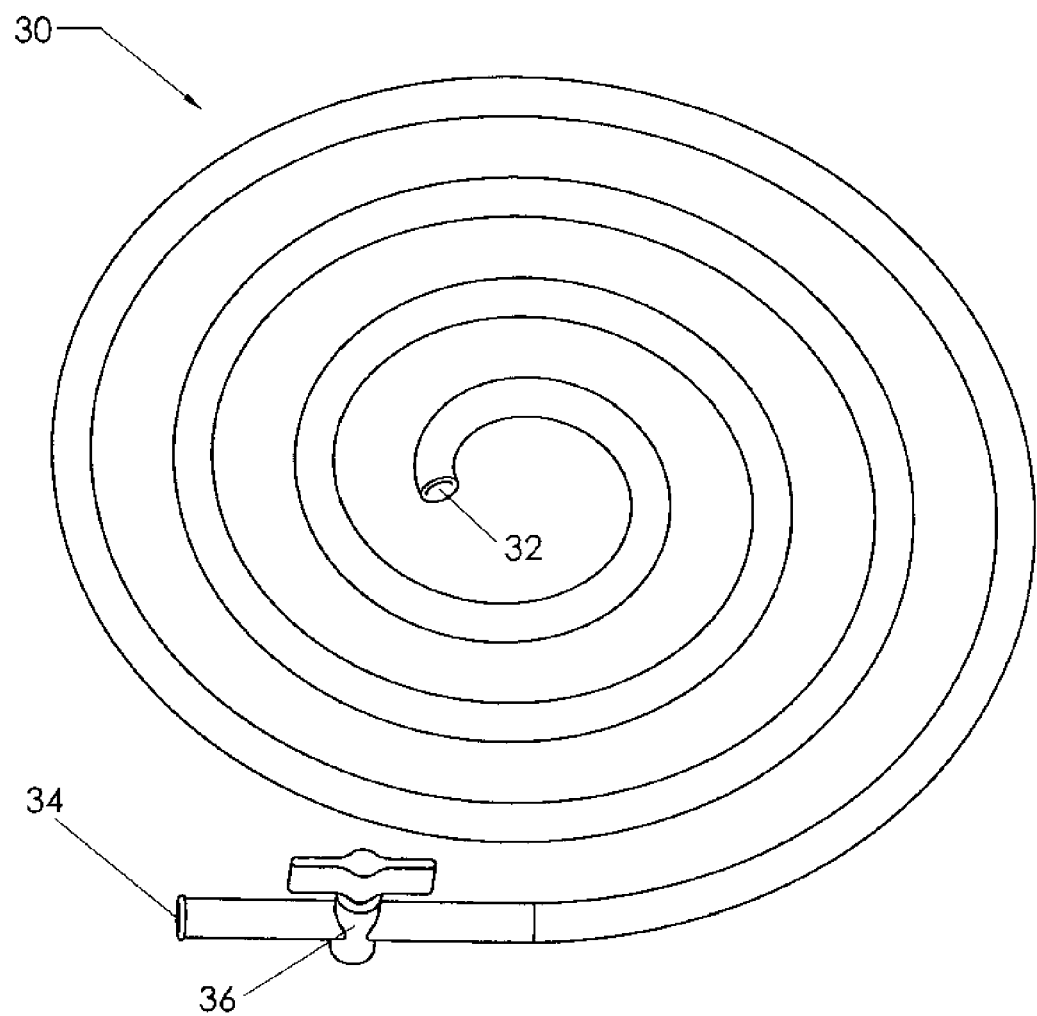
FIG. 5 is a panoramic view of the elongated polyethylene catheter of the invention, coiled for purposes of illustration.

The present invention is shown generally in the drawing figures, and that portion illustrated in FIGS. 1-6 consists of three separate parts:

The first part is a hollow, hard plastic cannula 10 with a small funnel 12 at its upper end, and an inclined or a sharp-pointed slant tip 14 at its low end. At the upper end of the plastic cannula, next to the small funnel, are two diametrically positioned rings 16 and 18 for better grasping, like holes of a scissors. The edge of the free border of the funnel 12 has one small notch 20 placed at mid-point between the two lateral rings 16 and 18.

The second part is a plastic plunger 22 whose shape mimics the configuration of the hollow inner-space of the cannula 10 and fits perfectly inside it, culminating in an inclined or a sharp tip 23 shaped to conform to the tip 14. It has a ring 24 at its upper engagement end, made of the same plastic material, attached and continuous with the flat upper surface 26 of the plunger 22. The flat surface 26 of the plunger 22 has a small protrusion 28 on the edge of the surface. This protrusion 28 fits perfectly in the notch 20 provided in the upper edge of the funnel 12, the notch 20 and protrusion 28 providing an alignment system.

The third part of this form of the invention is a long hollow polyethylene catheter 30 which ends freely at one end with a soft, smooth rounded tip 32. At the other end of the catheter, it is continuous with a female-type syringe connector 34, preceded by a flow control in the form of a stop-cock valve 36. This end of the catheter 30 is to be connected to the insufflating system of the Laparoscopy equipment (not illustrated, but conventional).

To perform an easy, safe quick and error-free abdominal insufflation, the surgeon has to first assess the thickness of the anterior abdominal wall by grasping its paniculus on both sides of the navel with the fingers and have a rough idea of its size. He then makes a longitudinal incision of approximately 6 mm, two centimeters above or below the navel, according to the nature of the Laparoscopic procedure. If the Laparoscopic procedure is in the upper abdomen, like a Cholecystectomy, the incision should be two centimeters below the navel, and vice versa. If the operation is in the lower abdomen, the incision for the cannula is done two cm above the navel.

Figure 6:
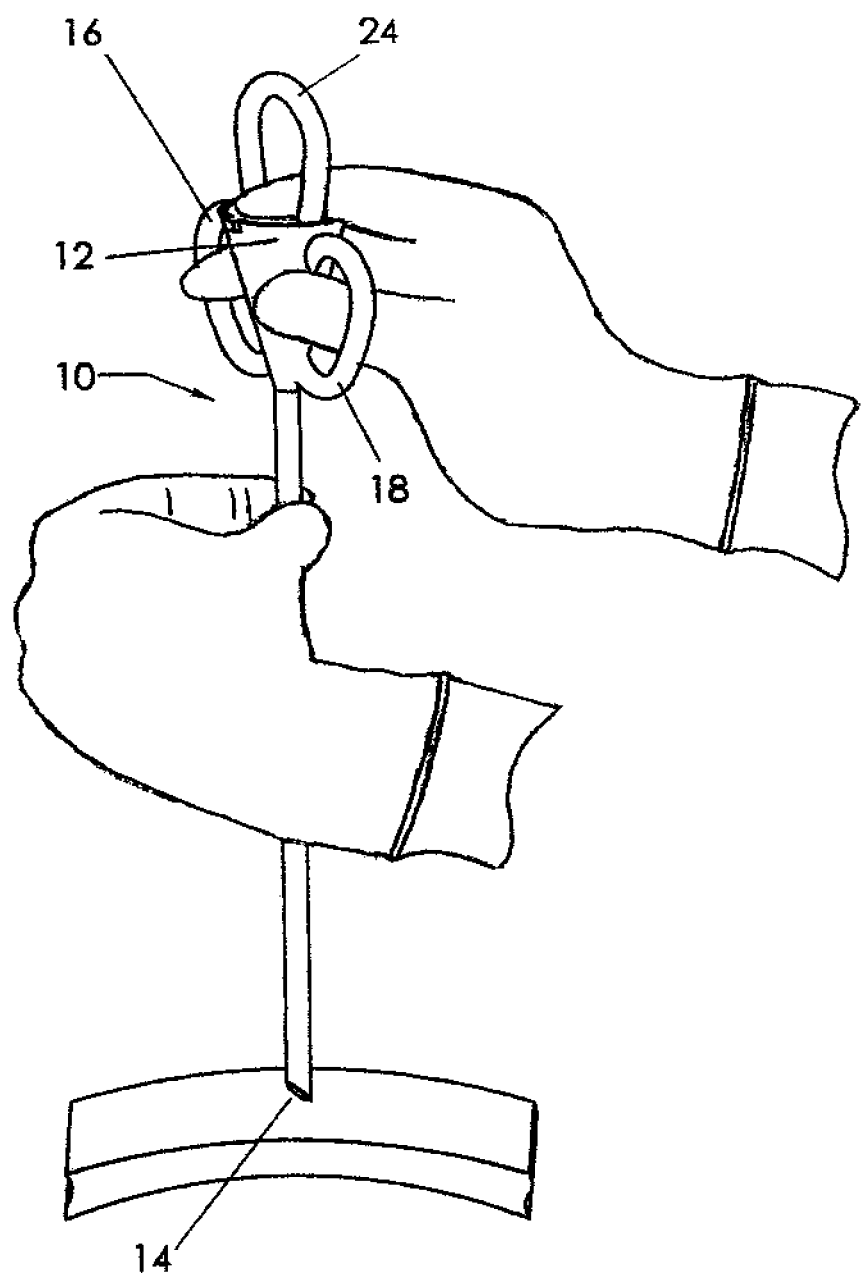
FIG. 6 shows the surgeon's hands appropriately holding the cannula and plunger while the surgeon traverses the thickness of the anterior abdominal wall around the navel.
Figures 10, 11, 12:
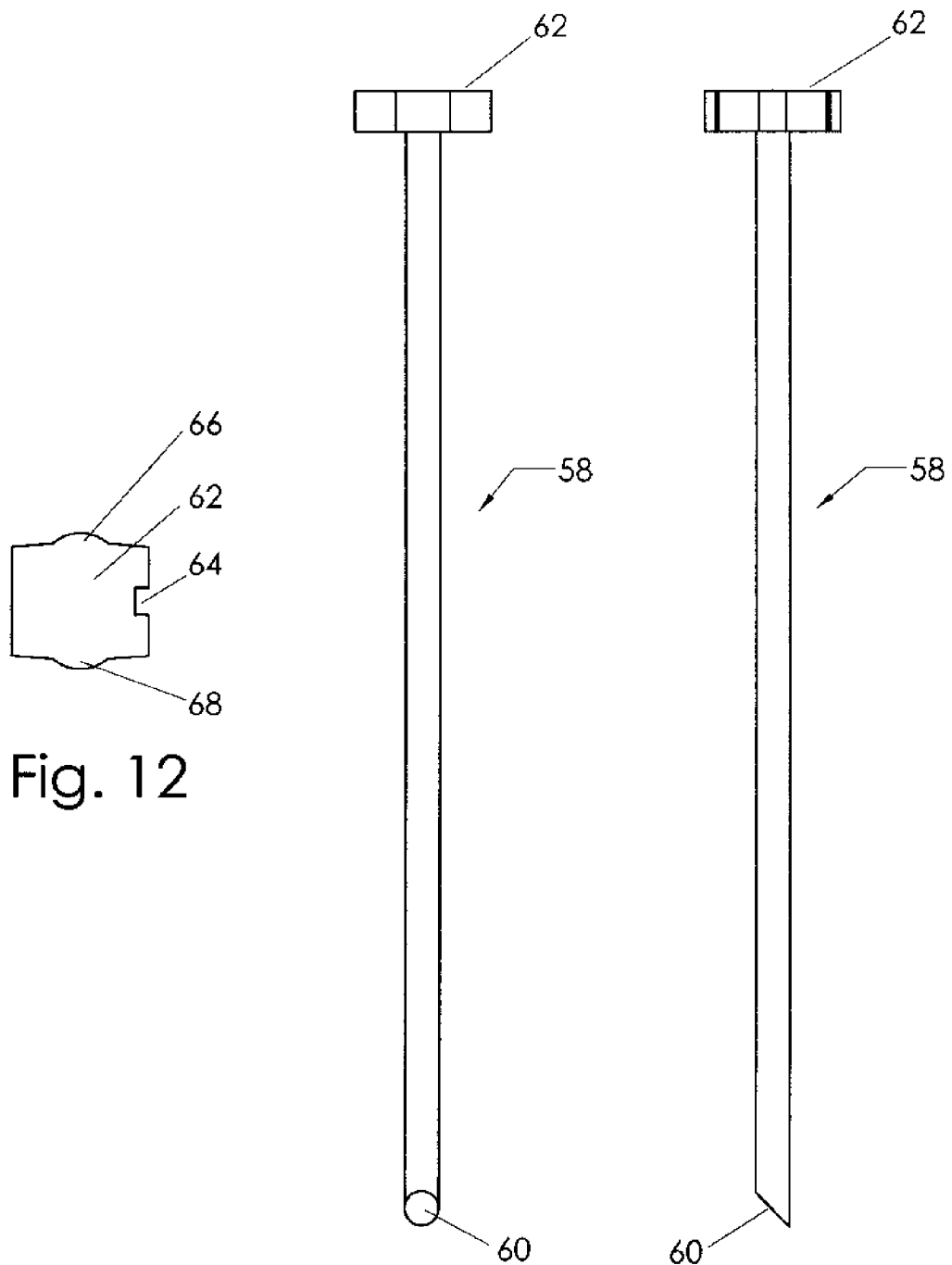
FIG. 10 is an elevational view of the cannula's plunger.
FIG. 11 is a side elevational view of the plunger of FIG. 10.
FIG. 12 is a top plan view of the plunger of FIG. 10.

The surgeon then asks his assistant to elevate as much as possible the umbilical area of the anterior abdominal wall with two towel clips placed two centimeters lateral to the incision. As shown in FIG. 6, he then holds the upper third of the cannula's stem with his left hand and inserts his middle finger inside one of the cannula's rings 18, and the thumb of the same hand inside the opposite ring 16. His index finger enters the guide ring 24 on top of the plunger 22 and presses it down to keep it in its position inside the cannula 10. When the plunger fits completely inside the cannula 10 it provides solidity to it, and in this way it prevents tissue or any other material from entering the cannula.

The surgeon then inserts vertically and slowly the plastic cannula 10 with its plunger 20 in place into the abdominal wall in a fashion similar to that employed for the insertion of the Veress needle. When the surgeon calculates that he has traversed approximately eighty percent of the anterior abdominal wall, he proceeds to advance the cannula-plunger unit by thrusting it, centimeter by centimeter, through the remainder twenty percent of the anterior abdominal wall's thickness. After every thrust, he removes the plunger 20 and inserts the polyethylene catheter 30 inside the cannula 10 and taps the bottom of the cannula 10 in a knocking fashion to see if it enters the abdominal cavity. If the catheter 30 doesn't go inside the abdominal cavity, he then removes the polyethylene catheter 30 and re-inserts the plunger 20. He thrusts down the cannula-plunger unit again one more centimeter and repeats the previously described knocking maneuver with the catheter 30 until it finds no resistance and freely enters the abdominal cavity.

The surgeon then proceeds to pass the polyethylene catheter 15 or 20 cm beyond the anterior abdominal wall. At this time the surgeon pulls back the plastic cannula 10 while he holds firmly with the other hand the polyethylene catheter 30 inside the abdomen. Next, his assistant releases the pull on the towel clips to allow the anterior abdominal wall to return to its resting position.

Successful insufflation of the abdomen can now be absolutely assured because the tip of the polyethylene catheter 30 lies freely and safely deep inside the abdominal cavity, more than fifteen centimeters beyond the formerly troublesome area, the anterior abdominal wall. Additionally, the soft, smooth, rounded end 32 of the polyethylene tube, combined with its slow, small-increments insertion through the anterior abdominal wall is devoid of the risk of injury to any internal organs as well as being incapable of creating pneumo-omentum.

In this form of the present invention, if the technique of insertion is followed as described, the sharp tip 14 of the cannula 10 should not reach more than one cm beyond the inner surface of the anterior abdominal wall and, consequently, could never injure anything inside the abdomen. The exception to this rule is the possibility of a bowel firmly attached to the anterior abdominal wall at the site of insertion of the cannula 10. This exceptional situation is easily avoided by not using a previous scar as the site for insertion of the cannula 10. The hesitancy, doubt, uncertainty and fear of failure that assail the surgeon are totally eliminated by the invention. Likewise, the trial and error associated with the insertion and re-insertion of the Veress needle through the abdominal wall until the surgeon thinks he is inside the free space of the abdominal cavity, is also eliminated. Once the abdominal wall has been sufficiently inflated, the polyethylene catheter 10 remains inside the abdomen while the subsequent steps of the operations go on.

Another advantage of the present invention over the Veress needle is as follows. When the abdominal cavity has been successfully inflated with the Veress needle, this needle is then totally removed from the abdomen. The same incision used for the Veress needle is then made larger to allow the insertion of the large Laparoscopic trocar. Once the Veress needle is out, the gas starts to decrease either by diffusion or by escape through the orifice left by the Veress needle. If the insertion of the large trocar is not successful the first time and the surgeon tries to re-insert it, the time involved in this process may allow the abdomen to deflate even more, making the subsequent attempts to insert the trocar significantly riskier. Contrary to the employment of the Veress needle, the site of insertion of the large trocar is far away from the one used by the polyethylene catheter 30 which lies safely inside the abdomen providing continuous abdominal insufflation. In case that the insertion of the large trocar is not successful, the abdominal cavity will never deflate. No matter how many times the surgeon tries to re-insert the trocar an additional advantage of the invention is that it can create a safe and effective pneumo-peritoneum without the need to do open Laparoscopies.

A second form for the invention is illustrated in FIGS. 7-13. This form of the invention is quite similar to that of FIGS. 1-6, with exceptions that will become apparent in the following description.

This form of the invention also consists of three parts, the first part being a hollow, hard plastic cannula 40 with a small funnel 42 at its upper end and an inclined tip 44 at its lower end. Similar to the first form of the invention, two diametrically opposed rings 46 and 48 are provided for better grasping. One of the rings has an extension 50 adjacent the edge of the funnel 42, as illustrated.

The cannula 40 has a helical external thread 52 having spaces 54 between thread convolutions. For determining depth of insertion, the cannula 40 can include numbers or other marking to represent depth, as illustrated in FIG. 7.

The funnel 42 has an internal cylindrical bore 56 extending the length thereof, from the tip 44 to the top of the funnel 42.

The plunger 58 is essentially identical to the plunger 22 of the first form of the invention, and fits in the bore 56. The plunger 58 has a tip 60 which is shaped to conform to the tip 44. The plunger has a head 62 which is essentially rectangular with a notch 64 in one of its sides corresponding to the protrusion 50. Wings 66 and 68 may be provided for manipulation of the plunger 58.

Figure 13:
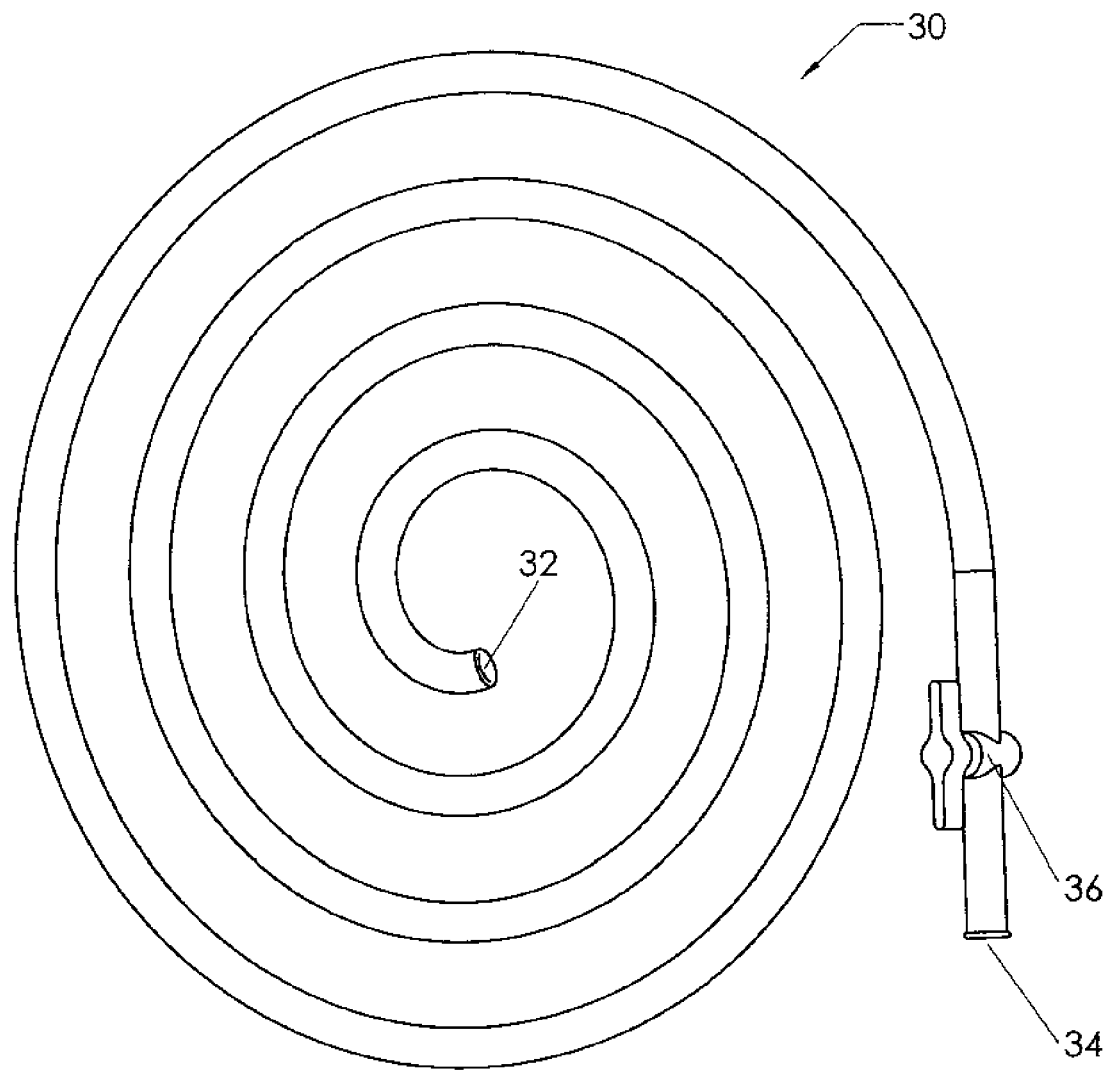
FIG. 13 is a panoramic view of the elongated polyethylene catheter of the invention, essentially similar to that shown in FIG. 5.

FIG. 13 illustrate the catheter used in combination with the cannula 40. The catheter is identical to the catheter 30 of FIG. 5, and is therefore not described in greater detail.

Figures 14, 15, 16:
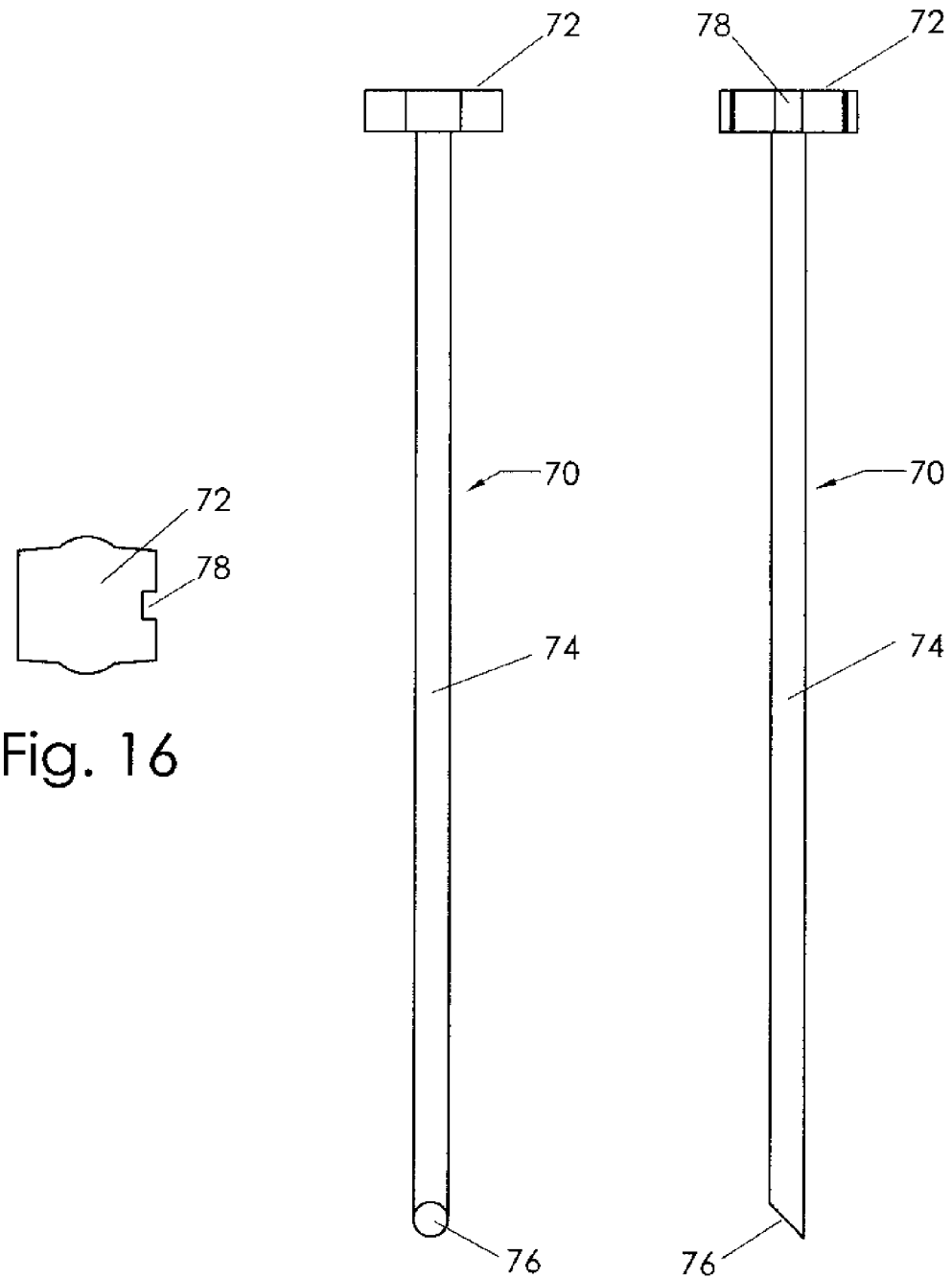
FIGS. 14, 15 and 16 are, respectively, front elevational, side elevational and top plan views of a plunger used with the cannula of FIGS. 17-24.

FIGS. 14-24 depict the abdominal trocar, also known as the principal trocar-cannula of the invention. FIGS. 14-16 illustrate the plunger for this form of the invention, FIGS. 17-19 illustrate the cannula for this form of the invention, and FIGS. 21-24 illustrate the one way valve for the cannula.

The plunger 70 is composed of two parts, a head 72 and a stem 74. The stem, opposite the head 72, terminates at a slanted tip 76 as illustrated. The head 72 includes a notch 78 on one side.

The cannula 80 of FIGS. 17-19 includes a tube 82 having an internal bore 84 shaped to accommodate insertion of the plunger 70. As illustrated, the tube 82 terminates, at its lower end, at a tip 86 shaped so that when the plunger 70 is inserted, the tip 76 of the plunger 70 and the tip 86 of the cannula 80 form a single, inclined tip.

The tube 82 has a helical thread 88 on its outer wall. The helical thread 88 is similar in form and function to the thread 52 of the cannula 40. And the helical thread 88 extend from proximate the tip 86 to a square collar 90.

Above the collar 90, a chamber 92, having extended wings 94 and 96, is located. The chamber 92 has a roof 98 with a central aperture 100. A sealing ring is embedded in the aperture 100.

Figure 20:
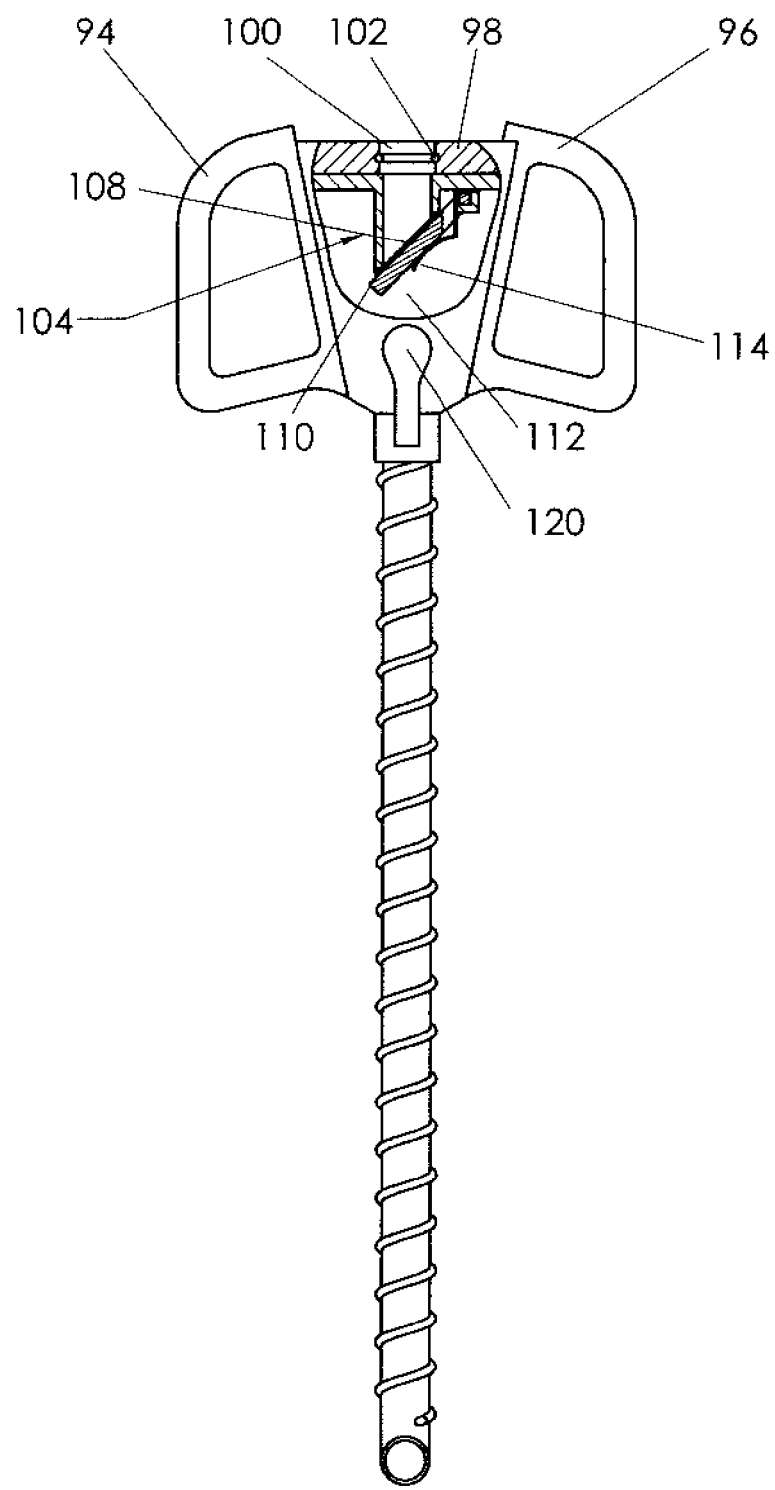
FIG. 20 is an elevational view similar to FIG. 17, but being cut away to show detail of a portion of the valve system for the cannula.
Figure 21:
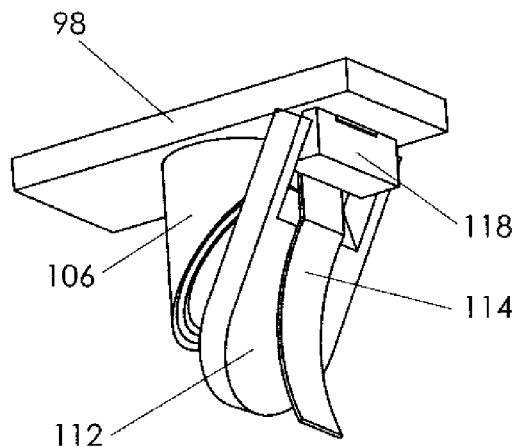
FIGS. 21-24 illustrate, in greater detail, the valve system shown in FIG. 20, and the parts thereof.
Figure 23:
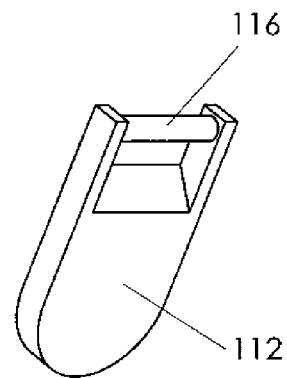
Figure 22:
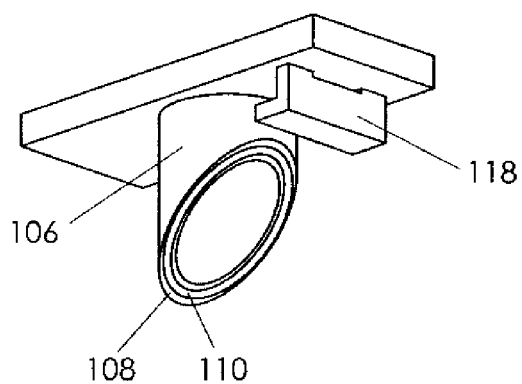
Figure 24:
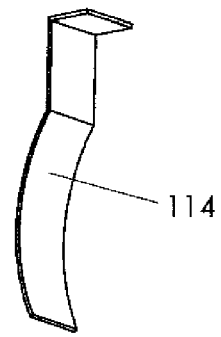

As best illustrated in FIG. 20, with parts illustrated in FIGS. 21-24, a one way valve 104 extends beneath the aperture 100. The valve 104 include a tube 106 with a slanted lower end 108 with a sealing ring 110 embedded in the lower end 108. A door 112, biased by a spring 114, closes against the slanted end 108, sealed by the ring 110. The door 112 includes a transverse rod 116, as best illustrated in FIG. 23, which fits beneath a bracket 118 on the underside of the roof 98. The spring 114 biases the door 112 in the closed position shown in FIG. 20.

The cannula 80 also includes a conventional on/off valve 120 communicating with the bore 84. The valve 120 can be turned on or off in a known manner in order to allow air to be expelled from the cannula 80.

The cannula 40 is used in a manner identical to that of the cannula 10 of FIGS. 1-6. However, its installation is slightly different. Once a patient is under anesthesia, an appropriate incision is made in the abdomen. The cannula 40, with the plunger 58 therewithin, is inserted in the incision, and the practitioner, using the helical thread 52, screws the cannula clockwise toward the abdominal cavity. The insertion is therefore by small increments, until the abdominal cavity is entered. By virtue of this gradual insertion, the operator is sure that the tip 44 will never be inserted beyond the inner surface of the abdominal wall. Thus, nothing inside the abdominal cavity can be injured. Once insertion has been completed, the plunger 58 is removed and the catheter 30 is inserted, as described above.

The cannula 80 is then installed. Abdomen has been distended through use of the catheter 30, an incision is made below the navel, and the cannula 80, with plunger 70 in place, is inserted inside the incision. Then, similar to installation of the cannula 40, the cannula 80, due to its helical thread, is screwed downwardly, until the surgeon determines that it has traversed about 80 percent of the thickness of the abdominal wall. The surgeon then proceeds to open the valve to see if gas escapes. If not, the surgeon continues to screw gradually further downwardly in small increments, opening the valve 120 after each interval. Once gas comes out the valve 120, the cannula 80 has been properly installed in the abdominal cavity. By advancing gradually in small increments, the surgeon is sure that the tip 86 will never be inserted too far beyond the inner surface of the abdominal wall. Thus, no intra-abdominal organs will be injured. Once the cannula 80 is in place, the plunger 70 is removed and any instrument to be used in the surgical procedure (not illustrated) can be passed through the port 84 to be used in a conventional fashion.

Various changes can be made to the invention which don't depart from the spirit thereof or scope of the following claims.

What is claimed is:

1. An abdominal insufflator, comprising
   a. an elongated, hollow cannula having an outer wall, an inclined tip at one end and an open opposite end,
   b. a solid plunger shaped to be engaged in and co-extensive with said cannula, said plunger having an inclined tip at one end and an engagement end shaped to conform to said open opposite end of said cannula so that, when said plunger is fully engaged in said cannula, said tips form a unitary inclined tip and said engagement end is seated in said open opposite end,
   c. a system for aligning said plunger when engaged within said cannula, and
   d. an external insertion thread formed on said outer wall of said cannula extending from proximate said tip.

2. The insufflator according to claim 1, in which said open opposite end is funnel-shaped.

3. The insufflator according to claim 2, in which said engagement end is funnel-shaped.

4. The insufflator according to claim 1, in which said aligning system comprises a notch in said open opposite end and a protrusion in said engagement end, said protrusion being shaped to fit within said notch.

5. The insufflator according to claim 1, including a pair of grasping rings located on opposite sides of said open opposite end.

6. The insufflator according to claim 1, including a guide ring at said engagement end.

7. The insufflator according to claim 1, including a catheter shaped to fit within said hollow cannula.

8. The insufflator according to claim 7, including a flow control for said catheter.

9. The insufflator according to claim 1, in which said cannula has an exterior insertion thread.

10. The insufflator according to claim 1 including marking on said cannula to represent depth.

11. An abdominal trocar, comprising,
    a. an elongated, hollow cannula having an outer wall, an inclined tip at one end and an opposite end,
    b. a solid plunger shaped to be engaged in and co-extensive with said cannula, said plunger having an inclined tip at one end and an engagement end shaped to conform to said opposite end of said cannula so that, when said plunger is fully engaged in said cannula, said tips form a unitary inclined tip and said engagement end is seated in said open opposite end,
    c. a system for aligning said plunger when engaged within said cannula,
    d. a valve system at said opposite end, and
    e. an external insertion thread formed on said outer wall of said cannula extending from proximate said tip.

12. The abdominal trocar according to claim 11, in which said valve system includes an inlet in alignment with and shaped to be engaged by said plunger.

13. The abdominal trocar according to claim 12, in which said inlet comprises a normally-closed valve.

14. The abdominal trocar according to claim 13, in which said normally-closed valve comprises a plunger-accommodating tube and a hinged lid engaging a seat to sealingly close said tube, and a spring urging said lid against said seat.

15. The abdominal trocar according to claim 11, in which said aligning system comprises a protrusion in said opposite end and a notch in said engagement end, said protrusion being shaped to fit within said notch.

16. The abdominal trocar according to claim 11, in which said valve system includes a normally-closed outlet valve.

17. The trocar according to claim 11 including marking on said cannula to represent depth.

18. An abdominal insufflator and abdominal trocar system, comprising
   a. an elongated, hollow first cannula having an inclined tip at one end and an open opposite end,
   b. a first solid plunger shaped to be engaged in and co-extensive with said first cannula, said plunger having an inclined tip at one end and an engagement end shaped to conform to said open opposite end of said first cannula so that, when said plunger is fully engaged in said cannula, said tips form a unitary inclined tip and said engagement end is seated in said open opposite end,
   c. a first system for aligning said first plunger when engaged within said first cannula,
   d. an elongated, hollow second cannula having an inclined tip at one end and an opposite end,
   e. a second solid plunger shaped to be engaged in and co-extensive with said second cannula, said plunger having an inclined tip at one end and an engagement end shaped to conform to said opposite end of said second cannula so that, when said plunger is fully engaged in said cannula, said tips form a unitary inclined tip and said engagement end is seated in said open opposite end,
   f. a second system for aligning said second plunger when engaged within said second cannula, and
   g. a valve system at said opposite end of said second cannula.

19. The system according to claim 18, in which at least one of said cannulas has an exterior insertion thread.

20. The system according to claim 19 including marking on at least one of said cannulas to represent depth.

* * * * *